United States Patent [19]

VandenBerg

[11] Patent Number: Plant 7,243

[45] Date of Patent: Jun. 5, 1990

[54] CHRYSANTHEMUM PLANT NAMED DANA

[75] Inventor: Cornelis P. VandenBerg, Salinas, Calif.

[73] Assignee: Yoder Brothers, Inc., Barberton, Ohio

[21] Appl. No.: 344,696

[22] Filed: Apr. 28, 1989

[51] Int. Cl.[5] ..... A01H 5/00

[52] U.S. Cl. ..... Plt./74

[58] Field of Search ..... Plt./74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Dana particularly characterized by its flat capitulum form, daisy capitulum type, white ray floret color, diameter across face of capitulum of up to 8 cm at maturity when grown as a pinched spray pot mum, uniform eight week photoperiodic flowering response to short days, medium plant height when grown as a pinched pot mum, and spreading branching pattern.

3 Drawing Sheets

The present invention comprises a new and distinct cultivar of Chrysanthemum, botanically known as *Dendranthema grandiflora,* and referred to by the cultivar name Dana.

Dana, identified as 83-813029, was originated from a cross made by Cornelis P. VandenBerg in a controlled breeding program in Salinas, Calif., in 1983.

The female parent of Dana was an unnamed seedling identified as 79-P73001. The male parent of Dana was an unnamed seedling identified as 80-100001.

Dana was discovered and selected as one flowering plant within the progeny of the stated cross by Cornelis P. VandenBerg in January of 1984, in a controlled environment in Salinas, Calif.

The first act of asexual reproduction of Dana was accomplished when vegetative cuttings were taken from the initial selection in March of 1984 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Dana are firmly fixed and are retained through successive generations of asexual reproduction.

Dana has not been observed under all possible environmental conditions. The phenotype may vary significantly with variations in environment such as temperature, light intensity and daylength.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Dana, which, in combination, distinguish this Chrysanthemum as a new and distinct cultivar:

1. Flat capitulum form.
2. Daisy capitulum type.
3. White ray floret color.
4. Diameter across face of capitulum up to 8 cm at maturity, when grown as a pinched spray pot mum.
5. Uniform eight week photoperiodic flowering response to short days.
6. Medium plant height, requiring 0 to 7 long days after pinch prior to short days and 1 application of 2500 ppm B-9 SP to attain a flowered plant height of 25 to 35 cm for year-round flowerings when grown as a pinched pot mum in a 15 cm pot.
7. Branching pattern is spreading.

The accompanying photographic drawings show typical inflorescence and leaf characteristics of Dana, with the colors being as nearly true as possible with illustrations of this type. Sheet 1 is a color photograph of Dana grown as a pinched spray pot mum grown in a 15 cm pot. Sheet 2 is a black and white photograph of three views of the inflorescence of Dana. Sheet 3 is a black and white photograph showing the upper and under sides of the leaves of Dana at three stages of development (mature, intermediate and immature).

Of the commercial cultivars known to the inventor, the most similar in comparison to Dana is Solo, disclosed in U.S. Plant Pat. No. 6,058. Reference is made to attached Chart A, which compares certain characteristics of Dana to the same characteristics of Solo.

Similar traits are capitulum form and type, branching pattern and plant height. Dana has a larger diameter across face of capitulum than Solo.

Dana has a slower controlled response than Solo. In the following description color references are made to The Royal Horticultural Society Colour Chart. The clear white color of the ray florets of Dana is not represented in the R.H.S. color chart. The color values were determined on plant material grown as a pinched spray pot mum in Salinas, Calif., on December 22, 1988.

Classification:

*Botanical.*—*Dendranthema grandiflora* cv Dana.
*Commercial.13* Daisy spray pot mum.

INFLORESCENCE

A. Capitulum:
*Form.*—Flat.
*Type.*—Daisy.
*Diameter across face.*—Up to 8 cm at maturity.

B. Corolla of Ray Florets:
*Color (general tonality from a distance of three meters).*—Clear white.
*Color (upper surface).*—Clear white.
*Color (under surface).*—Clear white.
*Shape.*—Straight, slightly concave, rounded petal tips.

C. Corolla of disc florets:

*Color* (*mature*).—13A.

*Color* (*immature*).—145A.

D. Reproductive organs:

*Androecium.*—Present on disc florets only; scant pollen.

*Gynoecium.*—Present on both ray and disc florets.

PLANT

A. General appearance:

*Height.*—Medium; 25 to 35 cm as a pinched spray pot mum with 0 to 7 long days after pinch prior to short days and 1 application of 2500 ppm B-9 SP.

B. Foliage:

*Color* (*upper surface*).—147A.

*Color* (*under surface*).—147B.

*Shape.*—Lobed.

CHART A

COMPARISON OF DANA AND SOLO

| | DANA | SOLO |
|---|---|---|
| Ray Floret Color | White | White |
| Capitulum Form and Type | Flat Daisy | Flat Daisy |
| Branching Pattern | Spreading | Spreading |
| Diameter Across Face of Capitulum | Up to 8 cm | 5 to 6 cm |
| Plant Height | Medium | Medium |
| Controlled Response | 8 weeks | 7 weeks |

Comparisons Made of Plants Grown As Pinched Spray Pot Mums In Salinas, California

I claim:

1. A new and distinct Chrysanthemum plant named Dana, as described and illustrated.

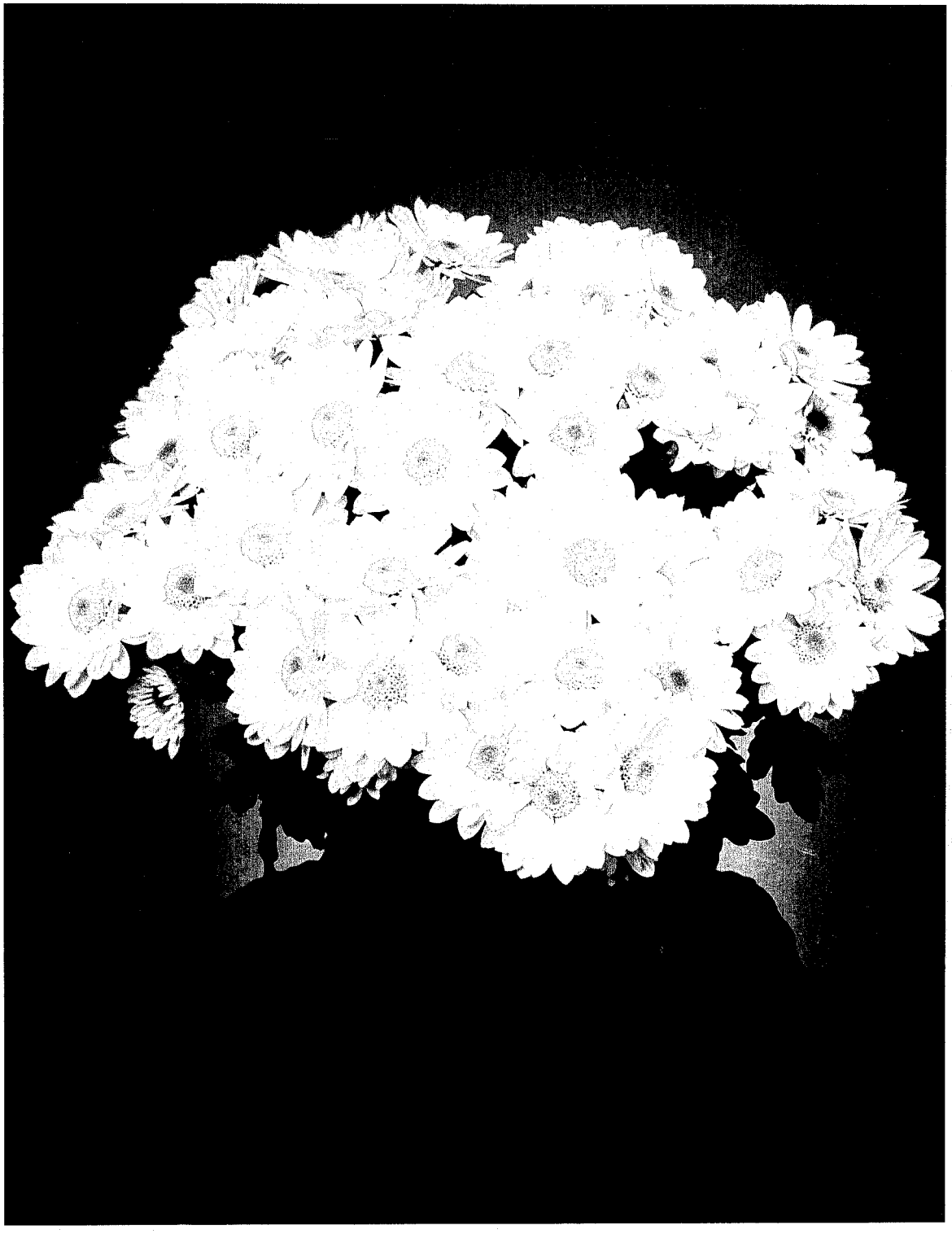

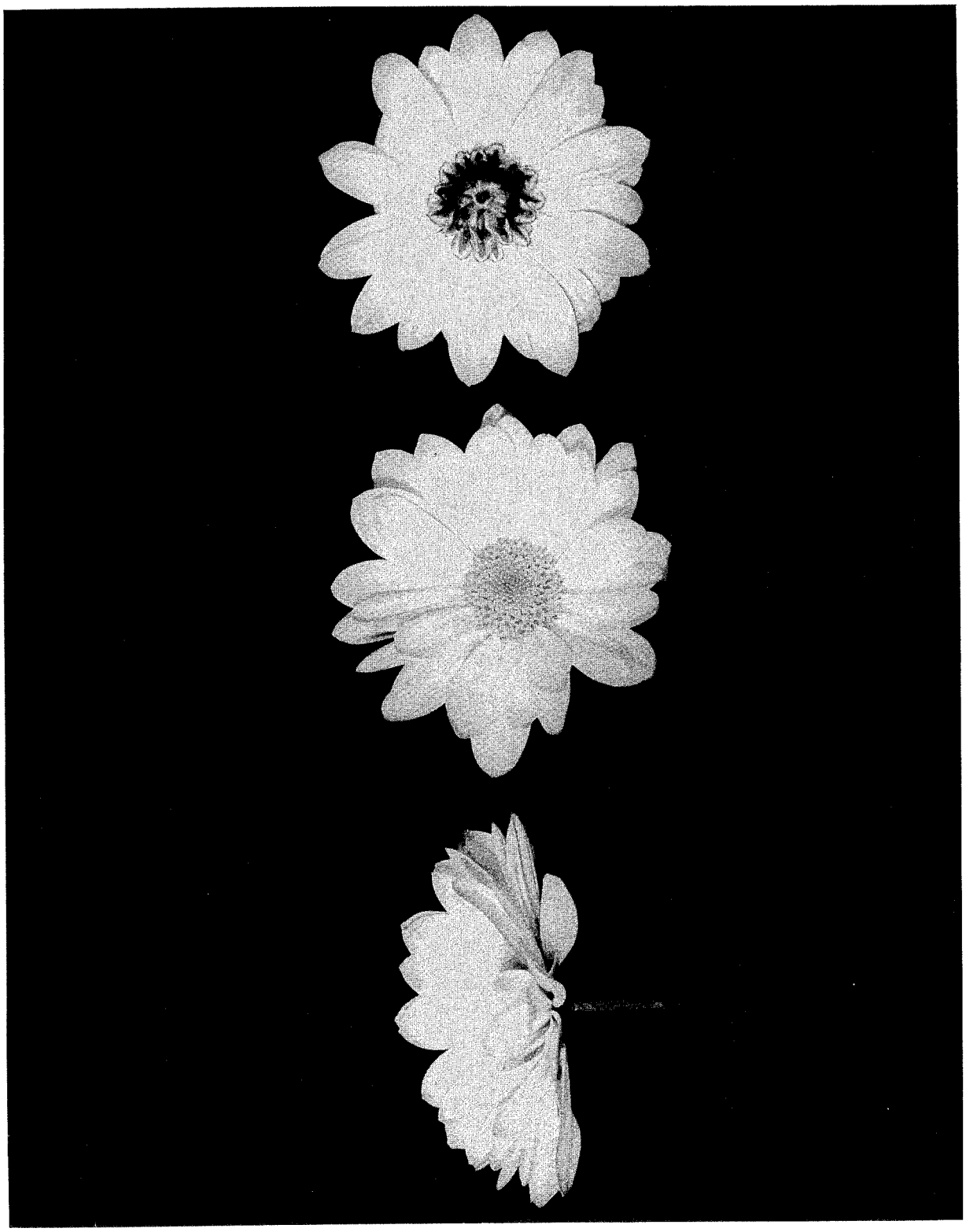

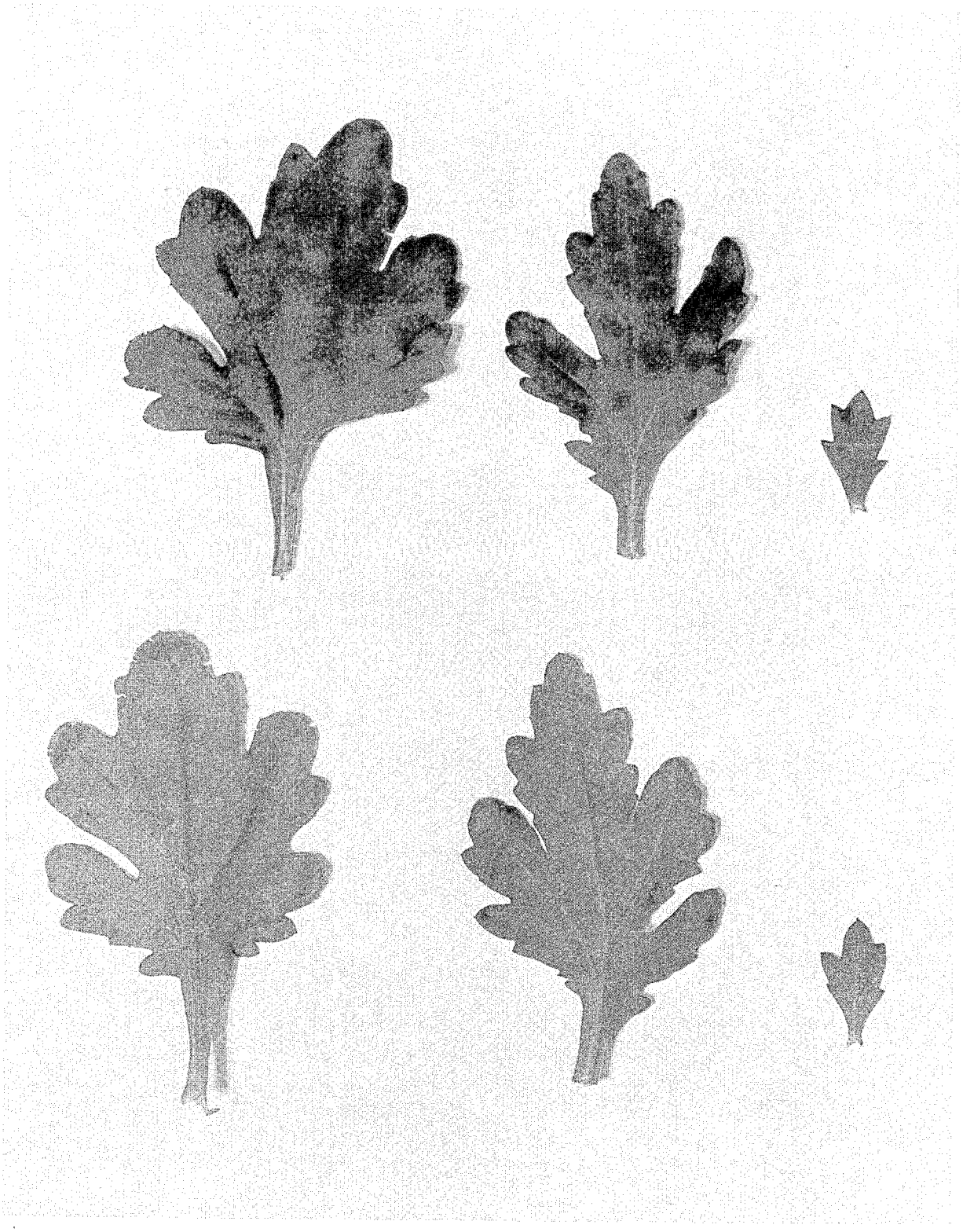

* * * * *